United States Patent [19]

Bollag et al.

[11] 4,187,247
[45] Feb. 5, 1980

[54] 9-SUBSTITUTED PHENYL-3,7-DIMETHYL-NONA 2,4,6,8-TETRAENE COMPOUNDS

[75] Inventors: Werner Bollag, Basel; Rüdolf Rüegg, Bottmingen; Gottlieb Ryser, Basel, all of Switzerland

[73] Assignee: Hoffmann-La Roche Inc., Nutley, N.J.

[21] Appl. No.: 19,025

[22] Filed: Mar. 8, 1979

Related U.S. Application Data

[62] Division of Ser. No. 903,639, May 8, 1978, Pat. No. 4,163,103, which is a division of Ser. No. 816,409, Jul. 18, 1977, Pat. No. 4,107,190, which is a division of Ser. No. 613,676, Sep. 15, 1975, Pat. No. 4,054,589.

[30] Foreign Application Priority Data

Sep. 26, 1974 [CH] Switzerland ............ 13032/74
Jul. 9, 1975 [CH] Switzerland ............ 8962/75

[51] Int. Cl.² .............. C07C 47/48; C07C 41/52; C07C 41/00

[52] U.S. Cl. .................. 260/574; 260/575; 260/577; 260/578; 260/599; 260/600 R; 568/584; 568/587; 568/588; 568/626; 568/648; 568/649; 568/812; 568/813; 424/333; 424/340; 424/341; 424/343; 424/330

[58] Field of Search ............ 260/599, 600 R, 574, 260/575, 577, 578; 568/584, 587, 588, 626, 648, 649, 812, 813

[56] References Cited

U.S. PATENT DOCUMENTS

| | | | |
|---|---|---|---|
| 2,451,738 | 10/1948 | Isler | 568/626 |
| 2,765,343 | 10/1956 | Benton | 260/600 X |
| 3,781,314 | 12/1973 | Bollag | 568/626 |
| 3,931,257 | 1/1976 | Pawson | 568/626 |

Primary Examiner—John F. Niebling
Attorney, Agent, or Firm—Jon S. Saxe; Bernard S. Leon; George W. Johnston

[57] ABSTRACT

Novel 9-substituted phenyl-3,7-dimethyl-nona-2,4,6,8-tetraene derivatives useful as anti-tumor agents.

1 Claim, No Drawings

9-SUBSTITUTED PHENYL-3,7-DIMETHYL-NONA 2,4,6,8-TETRAENE COMPOUNDS

This is a division of application Ser. No. 903,639 filed May 8, 1978 now U.S. Pat. No. 4,163,103, which in turn is a division of application Ser. No. 816,409, filed July 18, 1977, now U.S. Pat. No. 4,107,190, which in turn is a division of Ser. No. 613,676, filed Sept. 15, 1975, now U.S. Pat. No. 4,054,589.

SUMMARY OF THE INVENTION

In accordance with this invention, it has been discovered that the compounds of the formula:

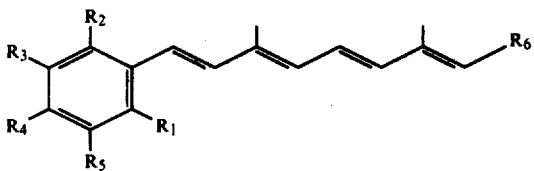

I wherein one of $R_1$ and $R_2$ is halogen or lower alkyl and the other is halogen or lower alkoxy; $R_3$ and $R_5$ are hydrogen, halogen or lower alkyl, with the proviso that one of $R_3$ and $R_5$ is other than halogen, $R_4$ is halogen, lower alkoxy, amino, mono(lower alkyl)amino or di(-lower alkyl) amino; and $R_6$ is formyl, hydroxymethyl, alkoxymethyl, alkanoyloxymethyl, carboxyl, alkoxycarbonyl, alkenyloxycarbonyl, alkynyloxycarbonyl, carbamoyl, mono(lower alkyl)carbamoyl, di(lower alkyl) carbamoyl or N-heterocyclylcarbonyl;

and salts thereof are useful as anti-tumor agents.

According to the process provided by the present invention, the compounds of formula I above and their salts are manufactured by reacting a compound of the formula:

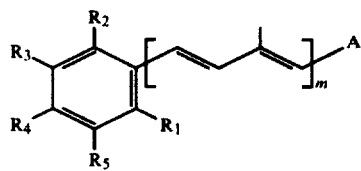

II with a compound of the formula:

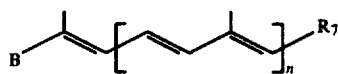

III wherein m is zero and n is 1, or m is 1 and n is zero, one of A and B is formyl and the other is either a triarylphosphoniummethyl group of the formula

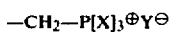
—CH$_2$—P[X]$_3$⊕Y⊖ in which X is aryl and Y is an anion of an organic or inorganic acid, or a dialkoxyphosphinylmethyl group of the formula

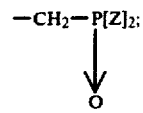

Z is alkoxy; or one of A and B is halomethyl, alkylsulphonyloxymethyl or arylsulphonyloxymethyl group and the other is a sulphonylmethyl group of the formula

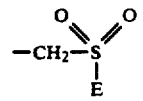

in which E is aryl or aralkenyl which may carry one or more electron-repelling to electron-weakly attracting substituents; $R_1$, $R_2$, $R_3$, $R_4$ and $R_5$ are as above; and $R_7$ is carboxyl, alkoxycarbonyl, alkenyloxycarbonyl, alkynyloxycarbonyl, di(lower alkyl)carbamoyl or N-heterocyclylcarbonyl; or when B is formyl, $R_7$ is carboxyl, alkoxycarbonyl, alkenyloxycarbonyl, alkynyloxycarbonyl, di(lower alkyl) carbamoyl, N-heterocyclylcarbonyl, alkoxymethyl or alkanoyloxymethyl; or when B is halomethyl, alkylsulfonyloxy or arylsulfonyloxy, $R_7$ is carboxyl, alkoxycarbonyl, alkenyloxycarbonyl, alkynyloxycarbonyl, di(lower alkyl) carbamoyl, N-heterocyclycarbonyl, formyl, alkoxymethyl or alkanoyloxymethyl; or when B is triarylphosphoniummethyl, dialkoxyphosphinylmethyl or sulphonylmethyl; $R_7$ is carboxyl, alkoxycarbonyl, alkenyloxycarbonyl, alkynyloxycarbonyl, di(lower alkyl)carbamoyl, N-heterocyclylcarbonyl or formyl;

and cleaving off a sulphone group which may be present in the reaction product to form an additional carbon-carbon bond, and, if desired, converting an acid obtained or an amine obtained into a salt, or converting a carboxylic acid of formula I into a carboxylic acid ester of formula I or into an amide of formula I, or converting a carboxylic acid ester of formula I into a carboxylic acid of formula I or into an amide of formula I, or reducing a carboxylic acid of formula I or a carboxylic acid ester of formula I to the corresponding alcohol of formula I and if desired etherifying or esterifying said alcohol, or saponifying an alcohol ester of formula I, or oxidising an alcohol or alcohol ester of formula I to the corresponding carboxylic acid.

DETAILED DESCRIPTION

The lower alkyl groups preferably contain from 1 to 6 carbon atoms such as methyl, ethyl, propyl, isopropyl or 2-methylpropyl. The lower alkoxy groups likewise preferably contain from 1 to 6 carbon atoms such as the methoxy, ethoxy or isopropoxy group.

The term "halogen" includes all four halogen groups such as chlorine, fluorine, bromine and iodine. Of the halogens, fluorine and chlorine are preferred.

The amino group can be monosubstituted or di-substituted by straight-chain or branched-chain lower alkyl groups, e.g., by methyl, ethyl or isopropyl.

The alkoxymethyl and alkoxycarbonyl groups preferably contain alkoxy groups having 1 to 6 carbon atoms. These can be straight-chain or branched-chain such as, for example, the methoxy, ethoxy or isopropoxy group. However, the alkoxy groups can also be higher alkoxy groups containing from 7 to 20 carbon atoms, especially the cetyloxy group. The said alkoxy groups can be substituted by functional groups; for example, by nitrogen-containing groups such as an optionally alkyl-substituted amino or morpholino group, or by a piperidyl or pyridyl group.

The alkenoxycarbonyl and alkynoxycarbonyl groups also preferably contain alkenoxy and alkynoxy groups containing from 2 to 6 carbon atoms such as, for example, the allyloxy or propargyloxy group.

The alkanoyl groups present in the alkanoyloxymethyl groups are preferably derived from lower alkanecarboxylic acids containing from 1 to 6 carbon atoms (e.g. acetic acid, propionic acid or pivalic acid), but they may also be derived from higher alkanecarboxylic acids containing from 7 to 20 carbon atoms (e.g. palmitic acid or stearic acid).

The carbamoyl group can be monosubstituted or di-substituted by straight-chain or branched-chain lower alkyl groups (e.g. methyl, ethyl or isopropyl). Examples of such substituted carbamoyl groups are the methylcarbamoyl, dimethylcarbamoyl and diethylcarbamoyl groups.

The N-heterocyclyl portion of the N-heterocyclylcarbonyl groups is preferably a 5-membered or 6-membered heterocyclic group which, in addition to the nitrogen atom, may also contain an oxygen or sulphur atom or a further nitrogen atom. Examples thereof are the piperidino, morpholino, thiomorpholino or pyrrolidino group.

Examples of compounds of formula I are:
9-(6-chloro-4-methoxy-2,3-dimethyl-phenyl)-3,7-dimethyl-nona-2,4,6,8-tetraen-1-oic acid ethyl ester;
9-(6-chloro-4-methoxy-2,5-dimethyl-phenyl)-3,7-dimethyl-nona-2,4,6,8-tetraen-1-oic acid ethyl ester;
9-(2-chloro-4-methoxy-3,5,6-trimethyl-phenyl)-3,7-dimethyl-nona-2,4,6,8-tetraen-1-oic acid ethyl ester;
9-(5-chloro-2,4-dimethoxy-6-methyl-phenyl)-3,7-dimethyl-nona-2,4,6,8-tetraen-1-oic acid ethyl ester;
9-(2,6-dichloro-4-methoxy-phenyl)-3,7-dimethyl-nona-2,4,6,8-tetraen-1-oic acid ethyl ester;
9-(2,5,6-trichloro-4-methoxy-phenyl)-3,7-dimethyl-nona-2,4,6,8-tetraen-1-oic acid ethyl ester;
9-(6-methyl-2,4-dimethoxy-phenyl)-3,7-dimethyl-nona-2,4,6,8-tetraen-1-oic acid ethyl ester; and
9-(2,4-dimethoxy-3,6-dimethyl-phenyl)-3,7-dimethyl-nona-2,4,6,8-tetraen-1-oic acid ethyl ester.

The aryl groups denoted by the symbol X in the triarylphosphoniummethyl groups formulated earlier include all generally known aryl groups. However, the aryl groups are preferably mononuclear aryl groups such as phenyl or (lower alkyl)- or (lower alkoxy)-substituted phenyl groups (e.g. tolyl, xylyl, mesityl and p-methoxyphenyl). Of the inorganic acid anions denoted by the symbol Y, the chlorine, bromine or iodine ion or the hydrosulphate ion is preferred. Of the organic acid anions, the tosyloxy ion is preferred.

The alkoxy groups denoted by the symbol Z in the dialkoxyphosphinylmethyl groups are preferably lower alkoxy groups containing from 1 to 6 carbon atoms, especially methoxy and ethoxy groups.

Examples of aryl or aralkenyl groups, which may carry one or more electron-repelling to electron-weakly attracting substituents on the aryl moiety and which is denoted by the symbol E in the sulphonylmethyl groups, are phenyl and styryl, both of which may be substituted in the o-, m- and/or p-position by methoxy, phenoxy, acetoxy;
dimethylamino, phenylmethylamino, acetylamino;
thiomethyl, thiophenyl, thioacetyl;
chloro, bromo;
cyano; or
nitro in the m-position.

Among the preferred compounds of formula II are compounds of the formula:

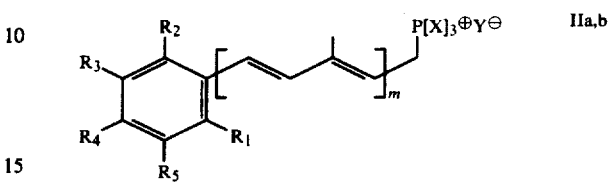

IIa,b wherein m is zero or 1; one of the $R_1$ and $R_2$ is halogen or lower alkyl and the other is halogen or lower alkoxy; one of $R_3$ and $R_5$ are hydrogen, halogen or lower alkyl; with the proviso that one of $R_3$ and $R_5$ is other than halogen; $R_4$ is halogen, lower alkoxy, amino, mono(-lower alkyl) amino, or di(lower alkyl)amino; X is aryl and Y is an anion of an organic or inorganic acid; and a compound of the formula:

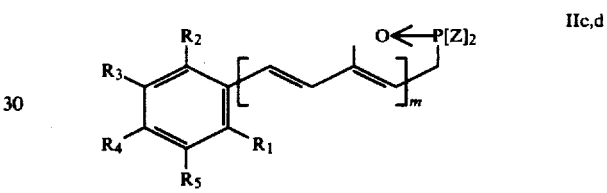

IIc,d wherein m is zero or 1; $R_1$ and $R_2$ is halogen or lower alkyl and the other is halogen or lower alkoxy; $R_3$ and $R_5$ are hydrogen, halogen or lower alkyl with the proviso that one of $R_3$ and $R_5$ is other than halogen, $R_4$ is halogen, lower alkoxy, amino, mono(lower alkyl)amino or di(lower alkyl) amino; and Z is alkoxy; and a compound of the formula:

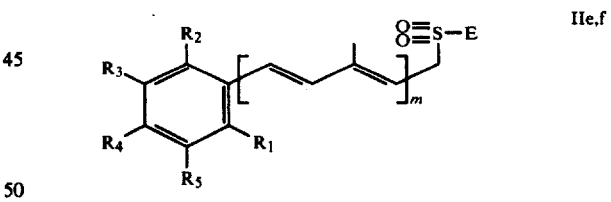

IIe,f wherein m is zero or 1; one of $R_1$ and $R_2$ is halogen or lower alkyl; and the other is halogen or lower alkoxy; $R_3$ and $R_5$ are hydrogen, halogen or lower alkyl; with the proviso that one of $R_3$ and $R_5$ is other than halogen; $R_4$ is halogen, lower alkoxy, amino, mono(lower alkyl) amino or di(lower alkyl)amino and E is aryl or aralkenyl; said aryl or aralkenyl may be unsubstituted or substituted with one or more electron-repelling to electron-weakly attracting substituents on the aryl moiety.

The starting materials of formula II, are, in part, novel and such novel starting materials also form part of this invention. They can be prepared, for example, in the following manner:

Compounds of formula II in which m is zero and A is triphenylphosphonium methyl group [II-a] or a dialkoxyphosphinylmethyl group [IIc] can be prepared, for example, by treating a corresponding ($R_1$–$R_5$)-benzene with formaldehyde in the presence of a hydrohalic acid (e.g. in the presence of concentrated hydrochloric acid optionally in a solvent, especially in a glacial acetic acid) and reacting the resulting ($R_1$-$R_5$)-benzyl halide [a halide of formula II in which the m is zero and A is halomethyl (IIi)] in a manner known per se with a triarylphosphine in a solvent, preferably with triphenylphosphine in toluene or benzene, or with trialkylphosphite, especially with triethylphosphite.

An alkoxy group can be introduced into the aforementioned ($R_1$-$R_5$)-benzene by, for example, alkylation of a hydroxy group already present. For example, the corresponding phenol, preferably in a solvent (e.g. an alkanol) and in the presence of a base (e.g. potassium carbonate) can be reacted with an alkyl halide (e.g. methyl iodide) or dimethylsulphate.

Compounds of the formula II in which m is 1 and A is triarylphosphonium methyl group [IIb] or a dialkoxyphosphinylmethyl group (IId) can be prepared, for example, in the following manner: A corresponding ($R_1$-$R_5$)-benzene is first subjected to formulation; for example, by allowing a formylating agent to act on said ($R_1$-$R_5$)-benzene. This can be carried out, for example, by carrying out the formylation in the presence of a Lewis acid. As formulating agents, there may be mentioned, in particular, orthoformic acid esters, formyl chloride and dimethylformamide. Especially suitable Lewis acids are the halides of zinc, aluminium, titanium, tin and iron, such as zinc chloride, aluminium trichloride, titanium tetrachloride, tin tetrachloride and ion trichloride, as well as the halides of inorganic and organic acids such as, for example, phosphorus oxychloride and methanesulphonyl chloride.

If the formylating agent is present in excess, the formylation may be carried out without the addition of a further solvent. However, it is generally recommended to carry out the formylation in an inert solvent (e.g. nitrobenzene or a chlorinated hydrocarbon such as methylene chloride). The formylation can be carried out at temperature between 0° C. and the boiling point of the formylation mixture.

The ($R_1$-$R_5$)-benzaldehyde obtained can be subsequently converted in a manner known per se by condensation with acetone in the cold (i.e., at a temperature of about 0° C.-30° C.) in the presence of alkali (e.g. dilute aqueous sodium hydroxide) into a ($R_1$-$R_5$)-phenyl-but-3-en-2-one which can be converted into a corresponding ($R_1$-$R_5$)-phenyl-3-methyl-3-hydroxy-penta-4-en-1-yne in manner known per se by means of an organometallic reaction (e.g. a Grignard reaction with the addition of acetylene). The resulting tertiary acetylenic carbinol is subsequently partially hydrogenated in a manner known per se using a partly deactivated noble metal catalyst (Lindlar catalyst). The resulting tertiary ethylenic carbinol can be subsequently be converted into the desired phosphonium salt of formula IIb in which the symbol m stands for 1 under allylic rearrangement by treatment with a triarylphosphine, especially triphenylphosphine, in the presence of a mineral acid (e.g. a hydrogen halide such as hydrogen chloride or hydrogen bromide or sulphuric acid) in a solvent (e.g. benzene). The tertiary ethylenic carbinol can also be halogenated to give a halide of the formula II in which m is 1 and A is halomethyl group (IIk) and the halide can be converted with a trialkylphosphite (e.g. triethylphosphite) into a corresponding phosphonate of the formula IId.

Compounds of formula II in which the symbol m is zero and A is sulphonylmethyl [IIe] can be prepared, for example, by dissolving a ($R_1$-$R_5$)-phenyl or a corresponding halobenzene in a polar solvent (e.g. an alkanol such as methanol, ethanol or isopropanol, tetrahydrofuran, dimethylformamide or glacial acetic acid) and treating the solution at room temperature with a sulphinic acid of the formula:

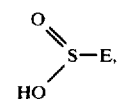

in which the symbol E has the significance given earlier, or with an alkali salt of said sulphinic acid. The sulphone can be isolated from the reaction mixture by, for example, making the reaction mixture neutral by the addition of an aqueous sodium bicarbonate solution and extracting the sulphone with an organic solvent (e.g. ethyl acetate or ether).

Compounds of formula II in which m is 1 and A is sulphonylmethyl [IIf] can be prepared in an analogous manner by reacting a ($R_1$-$R_5$)-phenyl-3-methyl-penta-2,4-dien-1-ol or a corresponding halide with a previously described sulphinic acid or with an alkali metal salt thereof.

Compounds of formula II in which m is zero and A is formyl [IIg] can be prepared, for example, by formylating a ($R_1$-$R_5$)-benzene in the manner previously described. In this manner, there is obtained directly the ($R_1$-$R_5$)-benzaldehyde.

Compounds of formula II in which m is 1 and A is formyl (IIh) can be prepared, for example, by reacting a ($R_1$-$R_5$)-phenyl-but-3-en-2-one (described hereinbefore in connection with the preparation of compounds of formula IIb) under the conditions of a Wittig reaction with ethoxycarbonyl-methylene-triphenyl-phosphorane or with diethyl-phosphonacetic acid ethyl ester. The resulting ($R_1$-$R_5$)-phenyl-3-methyl-penta-2,4-dien-1-oic acid ethyl ester is subsequently reduced in the cold by means of a mixed metal hydride, especially lithium aluminium hydride, in an organic solvent (e.g. ether or tetrahydrofuran) to give a ($R_1$-$R_5$)-phenyl-3-methyl-penta-2,4-dien-1-ol. This alcohol is then oxidised by treatment with an oxidising agent (e.g. manganese dioxide in an organic solvent such as acetone or methylene chloride) at a temperature between 0° C. and the boiling point of the oxidation mixture to give the desired ($R_1$-$R_5$)-phenyl-3-methyl-penta-2,4-dien-1-al of formula IIh.

The compounds of the formula III are, in part, novel.

Compounds of formula III in which the symbol n is zero and B is triarylphosphoniummethyl [IIIa] or a dialkoxyphosphinylmethyl group [IIIc] can be readily prepared by reacting a 4-halo-3-methyl-crotonic acid, which may be esterified, or an etherified 4-halo-3-methyl-crotyl alcohol with a triarylphosphine in a solvent, preferably with triphenylphosphine in toluene or benzene, or with a trialkylphosphite, especially with triethylphosphite.

Compounds of formula III in which n is 1 and B is triarylphosphoniummethyl [IIIb] or dialkoxyphosphinylmethyl [IIId] can be prepared, for example, by reducing the formyl group in an aldehyde of formula III, in which n is 1 and B is formyl [IIIh] to the hydroxymethyl group using a metal hydride such as sodium borohydride in an alkanol (e.g. ethanol or isopropanol). The resulting alcohol can be halogenated using a customary halogenating agent (e.g. phosphorous oxychloride) and the resulting 8-halo-3,7-dimethyl-octa-2,4,6-triene-1-carboxylic acid, a halide of formula III in which n is 1 and B is halomethyl [IIIk], or a derivative thereof can be converted with a triarylphosphine in a solvent, preferably triphenylphosphine, in toluene or benzene, or with a trialkylphosphite, especially triethylphosphite, into a desired phosphonium salt of formula IIIb or phosphonate of formula IIId.

Compounds of formula III in which n is zero and B is sulphonylmethyl [IIIe] can be prepared, for example, by reacting 4-hydroxy-3-methyl-but-2-en-1-al or the acetate thereof or the corresponding bromide in a polar solvent (e.g. isopropanol or n-butanol) in the manner previously described with an aforementioned sulphinic acid or with an alkali metal salt thereof.

Compounds of formula III in which n is 1 and B is sulphonylmethyl [IIIf] can be prepared in a manner analogous to that previously described by the reaction of, for example, 8-hydroxy-3,7-dimethyl-octa-2,4,6-trien-1-oic acid or the acetate thereof or a corresponding bromide with an aforementioned sulphinic acid.

Compounds of formula III in which n is zero and B is formyl [IIIg] can be prepared, for example, by oxidatively cleaving an optionally esterified tartaric acid (e.g. using lead tetraacetate at room temperature in an organic solvent such as benzene). The glyoxalic acid derivative obtained is subsequently condensed in a manner known per se, conveniently in the presence of an amine, with propionaldehyde at an elevated temperature (e.g. a temperature between 60° C. and 110° C.) with loss of water to give a desired 3-formyl-crotyl alcohol derivative.

Compounds of formula III in which n is 1 and B is formyl [IIIh] can be prepared, for example, by allowing phosgene to act on 4,4-dimethoxy-3-methyl-but-1-en-3-ol in the cold, preferably at −10° C. to −20° C. in the presence of a tertiary amine such as pyridine and condensing the resulting 2-formyl-4-chloro-but-2-ene under the conditions of a Wittig reaction with 3-formyl-crotonic acid, which may be esterified, or with a 3-formyl-crotyl alcohol, which may be esterified, to give the desired aldehyde of formula IIIh.

In accordance with the process provided by the present invention, a phosphonium salt of formula IIa or IIb is reacted with an aldehyde of formula IIIh or IIIg, or a phosphonium salt of formula IIIa or IIIb is reacted with an aldehyde of formula IIh or IIg, or a phosphonate of formula IIc or IId is reacted with an aldehyde of formula IIIh or IIIg, or a phosphonate of formula IIIc or IIId is reacted with an aldehyde of formula IIh or IIg, or a sulphone of formula IIe or IIf is reacted with a halide of formula IIIk or IIIi or a sulphone of formula IIIe or IIIf is reacted with a halide of formula IIk or IIi.

According to the Wittig procedure, the components are reacted with one another in the presence of an acid-binding agent (e.g., an alkali metal alcoholate such as sodium methylate or an alkylene oxide which may be alkyl-substituted, especially ethylene oxide or 1,2-butylene oxide), or if desired in a solvent (e.g. a chlorinated hydrocarbon such as methylene chloride, or dimethylformamide), at a temperature between room temperature and the boiling point of the reaction mixture.

According to the Horner procedure, the components are reacted together using a base and preferably in the presence of an inert organic solvent, for example, sodium hydride in benzene, toluene, dimethylformamide, tetrahydrofuran or 1,2-dimethoxyethane, or also sodium methylate in methanol, at a temperature between 0° C. and the boiling point of the reaction mixture.

According to the Julia procedure, the components are reacted with one another using a condensation agent, conveniently in the presence of a polar solvent. Suitable solvents are, for example, dimethylformamide, dimethyl sulphoxide, dimethylacetamide, tetrahydrofuran and hexamethylphosphoric acid triamide as well as alcohols such as methanol, isopropanol or terbutanol. Of the strong bases which are particularly useful as the condensation agents there can be mentioned, for example, alkali metal and alkaline earth metal carbonates, especially sodium carbonate, alkali metal hydroxides such as potassium hydroxide or sodium hydroxide, alkali metal and alkaline earth metal alcoholates such as sodium methylate and, especially, potassium tertbutylate, alkali metal hydrides such as sodium hydride, alkylmagnesium halides such as methyl-magnesium bromide and alkali metal amides such as sodium amide. The reaction using this procedure is preferably carried out at a low temperature, especially at a temperature below the freezing point (e.g. between −50° C. and −80° C.).

It has been found to be convenient in certain cases to carry out the aforementioned reactions in situ; that is to say, without isolating the particular phosphonium salt, phosphonate or sulphone from the medium to which it is prepared.

A carboxylic acid of formula I can be converted in a manner known per se (e.g. by treatment with thionyl chloride, preferably in pyridine) into an acid chloride which can be converted into an ester by reaction with an alkanol and into an amide by reaction with ammonia.

A carboxylic acid ester of formula I can be hydrolysed to a carboxylic acid in a manner known per se; for example, by treatment with an alkali, especially aqueous-alcoholic sodium hydroxide or potassium hydroxide at a temperature between room temperature and the boiling point of the mixture. The resulting carboxylic acid can then be amidated via an acid halide. Alternatively, a carboxylic acid ester can be directly amidated as described hereinafter.

A carboxylic acid ester of formula I can be converted directly into a corresponding amide by treatment with lithium amide. This treatment is advantageously carried out at room temperature.

A carboxylic acid or a carboxylic acid ester of formula I can be reduced to a corresponding alcohol of formula I in a manner known per se. The reduction is advantageously carried out using a metal hydride or alkyl metal hydride in an inert solvent. Examples of hydrides which have proved to be particularly suitable are metal hydrides such as lithium aluminum hydride and bis-[methoxy-ethylenoxy]-sodium aluminium hydride. Suitable inert solvents are, inter alia, ether, tetrahydrofuran or dioxane when lithium aluminium hydride is used and ether, hexane, benzene or toluene when diisobutylaluminium hydride or bis-[methoxy-ethylenoxy]-sodium aluminium hydride is used.

An alcohol of formula I can be etherified with an alkyl halide (e.g. ethyl iodide), for example in the presence of a base, preferably sodium hydride, in an organic solvent such as dioxane, tetrahydrofuran, 1,2-dimethoxyethane or dimethylformamide, or in the presence of an alkali metal alcoholate in an alkanol, at a temperature between 0° C. and room temperature.

An alcohol of formula I can also be esterified by treatment with an alkanoyl halide or anhydride, expediently in the presence of a base (e.g. pyridine or triethylamine) at a temperature between room temperature and the boiling point of the mixture.

An alcohol ester obtained can be saponified in a manner known per se; for example in the manner previously described in connection with the saponification of a carboxylic acid ester.

An alcohol of formula I or an ester thereof can be oxidised in a manner known per se to give a corresponding acid of formula I. The oxidation is advantageously carried out using silver (I) oxide an alkali in water or in a water-miscible organic solvent at a temperature between room temperature and the boiling point of the mixture.

An amine of formula I forms acid addition salts with inorganic acids (e.g. hydrohalic acids, especially hydrochloric acid or hydrobromic acid, and sulphuric acid) and with organic acids (e.g. benzoic acid, acetic acid, citric acid and lactic acid). A carboxylic acid of formula I forms salts with bases, especially with alkali metal hydroxides and particularly with sodium hydroxide and potassium hydroxide.

The compounds of formula I can occur as a cis/trans mixture which may be separated in a manner known per se into the cis and trans components or isomerised in a manner known per se to the all-trans compounds.

The present polyene compounds of formula I are pharmacodynamically valuable. They are effective in regressing the growth of tumors such as papillomas.

The compounds of formula I are also useful as medicaments for the topical and systemic therapy of acne, psoriasis and other related dermatological disorders which are characterized by an increased or pathologically altered cornification, as well as inflammatory and allergic dermatological conditions. They can also be used to treat disorders which are characterized by inflammatory or degenerative alterations of the mucous membranes.

The toxicity of the present polyene compounds is slight. For example, when 9-(2-chloro-4-methoxy-3,5,6-trimethyl-phenyl)-3,7-dimethyl-nona-2,4,6,8-tetraen-1-oic acid is administered intraperitoneally to mice weighing 30 g. in a daily dosage of 200 mg/kg, then no indication of an A-hypervitaminosis becomes evident after 14 days [total of 10 administration days].

The first indications of a light A-hypervitaminosis in mice appears at a daily dosage of 400 mg/kg after 14 days [total of 10 administration days]. This manifests itself in a weight decrease of 20%, a moderate hair loss and slight flaking of the skin.

The tumour-inhibiting activity of the present polyene compounds is significant. In the papilloma test, tumours induced with dimethylbenzanthracene and croton oil regress. The diameter of the papillomas within 2 weeks after the intraperitoneal administration of 9-(2-chloro-4-methoxy-3,5,6-trimethyl-phenyl)-3,7-dimethyl-nona-2,4,6,8-tetraen-1-oic acid ethyl ester decreases by 61% at a dosage of 400 mg/kg/week and by 45% at a dosage of 200 mg/kg/week.

The polyene compounds of formula I and their salts can therefore be used as medicaments; for example, in the form of pharmaceutical preparations which contain them in association with a compatible pharmaceutical carrier.

The pharmaceutical preparations for systemic administration can be prepared, for example, by adding a polyene compound as the active ingredient to non-toxic inert solid or liquid carriers which are usual in such preparations.

The pharmaceutical preparations can be administered enterally or parenterally. Suitable preparations for enteral administration are, for example, tablets, capsules, dragees, syrups, suspensions, solutions and suppositories and suitable preparations for parenteral administration are infusion and injection solutions.

The dosages in which the polyene compounds of this invention are administered can be varied according to the mode and route of administration and according to the requirements of the patient.

The polyene compounds of this invention can be administered in amounts of from 5 mg. to 200 mg. daily in one or more dosages. Capsules containing ca 10 mg. to ca 100 mg. of a polyene compound of this invention represent a preferred form of administration.

The pharmaceutical preparations can contain inert or pharmacodynamically active ingredients. Tablets or granules, for example, can contain a series of binders, fillers, carrier materials or diluents. Liquid preparations can, for example, take the form of a sterile water-miscible solution. Capsules can contain a filler or thickener. Furthermore, flavour-improving additives and substances commonly used as preservatives, stabilisers, moisture-retainers or emulsifiers, salts for varying the osmotic pressure, buffers and other additives can also be present in the pharmaceutical preparations.

The aforementioned carrier materials and diluents can be organic or inorganic substances such as water, gelatin, lactose, starch, magnesium stearate, talc, gum arabic, polyalkyleneglycols and the like. It is, of course, a prerequisite that all adjuvants used in the preparation of the pharmaceutical preparations are non-toxic.

For topical administration, the present polyene compounds are expediently made up in the form of ointments, tinctures, creams, solutions, lotiions, sprays, suspensions and the like. Ointments, creams and solutions are preferred. These pharmaceutical preparations for topical administration can be prepared by mixing the polyene compounds, as the active ingredient, with non-toxic inert solid or liquid carriers which are customary in such preparations and which are suitable for topical treatment.

Expedient for topical administration are ca 0.01% to ca 0.3% preferably 0.02% to 0.1%, solutions and ca 0.05% to ca 5%, preferably ca 0.1% to ca 2.0%, ointments or creams.

An antioxidant (e.g. tocopherol, N-methyl-v-tocopheramine, butylated hydroxyanisole or butylated hydroxytoluene) can also be present in the pharmaceutical preparations.

The compounds of formula I are utilized as salts with pharmaceutically acceptable acids and bases. These salts can be prepared utilizing conventional methods of preparing these salts.

The following Examples illustrate the present invention. In the Examples, the term "normal conditions" designates normal pressure and room temperature. The term "low boiling point petroleum ether" designates a fraction of petroleum ether boiling at 30° to 45° C. The term "5% palladium on carbon" designates a catalyst containing 5% by weight palladium on 95% by weight carbon. In the Examples, the ether utilized is diethyl ether and the temperature is in degrees Centrigrade (° C.).

EXAMPLE 1

9.9 g. of 2-chloro-4-methoxy-3,5,6-trimethyl-benzyl-triphenylphosphonium chloride are dissolved in 50 ml. of dimethylformamide. After the addition of 4.16 g. of 7-formyl-3-methyl-octa-2,4,6-trien-1-oic acid ethyl ester, the solution is treated dropwise at 20° C. with 10 ml. of a solution of sodium ethylate freshly prepared from 0.460 g. of sodium and 10 ml. of absolute ethanol. The mixture is stirred at room temperature for 12 hours, then introduced into 100 ml. of water and extracted with hexane. The hexane extract is shaken out three times with methanol/water, dried over sodium sulphate and evaporated under reduced pressure. The residue is purified by absorption on silica gel using methylene chloride/hexane (8:2 parts by volume) for the elution. The 9-(2-chloro-4-methoxy-3,5,6-trimethyl-phenyl)-3,7-dimethyl-nona-2,4,6,8-tetraen-1-oic acid ethyl ester obtained from the eluate melts at 90° C. after recrystallisation from hexane.

EXAMPLE 2

189 g. of 3-chloro-4,6-dimethyl-benzyl chloride are introduced into 1500 ml. of 5-N aqueous sodium hydroxide. The mixture is treated while stirring with 195 g. of zinc dust within 2 hours. The temperature of the reaction, which takes place exothermically, is maintained at 70° C. by cooling. The mixture is stirred for a further 12 hours at 50° C. and subsequently filtered. The filtrate is extracted three times with 800 ml. of ethylene chloride. The methylene chloride extract is washed neutral with water, dried over sodium sulphate and evaporated. The residual 2-chloro-3,5,6-trimethyl-benzene is purified by adsorption on silica gel using hexane/methylene chloride (9:1 parts by volume) for the elution. The compound boils at 81° C./9 mm Hg.

70 g. of 2-chloro-3,5,6-trimethyl-benzene are added dropwise within 30 minutes while stirring to 400 ml. of aqueous nitric acid [70% v/v] pre-cooled to 0° C. The mixture is stirred for a further 4 hours at a slowly increasing temperature up to 20° C., then introduced into ice-water and thoroughly extracted with diethyl ether. The ether extract is washed six times with 1000 ml. of water, dried over sodium sulphate and evaporated under reduced pressure. The residual 2-chloro-4-nitro-3,5,6-trimethylbenzene is purified by adsorption on silica gel using hexane/benzene (3:7 parts by volume) for the elution. The compound melts at 79° C. after recrystallisation from low-boiling petroleum ether.

114.5 g. of 2-chloro-4-nitro-3,5,6-trimethyl-benzene are dissolved in 300 ml. of ethyl acetate. The solution is diluted with 300 ml. of ethanol and, after the addition of 20 ml. of Raney-nickel, hydrogenated under normal conditions. After the uptake of 43 liters of hydrogen, the hydrogenation is terminated. The catalyst is filtered off while gassing with carbon dioxide and washed with ethanol. The combined filtrates are evaporated under reduced pressure. The residual 4-amino-2-chloro-3,5,6-trimethyl-benzene melts at 93° C. after recrystallisation from hexane.

65 g. of 4-amino-2-chloro-3,5,6-trimethyl-benzene are gradually introduced into 250 ml. of concentrated aqueous sulphuric acid while stirring and cooling. In so doing, the temperature rises to +60° C. The mixture is cooled to 0° C. by the gradual addition of 750 g. of ice and then treated dropwise within 3 hours with a solution of 26.4 g. of sodium nitrite in 80 ml. of water. The mixture is stirred for a further 90 minutes at 0° C. to +10° C. and subsequently filtered. The filtrate is subjected to a steam distillation while adding dropwise 600 ml. of aqueous sulphuric acid [50 vol%]. The distillate is extracted three times with 1000 ml. of methylene chloride. The methylene chloride extract is dried over sodium sulphate and evaporated. The residual 2-chloro-4-hydroxy-3,5,6-trimethyl-benzene melts at 97° C. after recrystallisation from hexane.

After the addition of 400 ml. of methanol and 85.5 ml. of dimethyl sulphate, 76 g. of 2-chloro-4-hydroxy-3,5,6-trimethyl-benzene are treated dropwise while stirring with 256.5 ml. of aqueous potassium hydroxide [25% g/v]. The mixture, which thereby heats to boiling, is stirred for a further 4 hours under reflux conditons and subsequently evaporated. The residue is taken up in 600 ml. of water. The aqueous solution is extracted three times with 600 ml. of diethyl ether. The ether extract is washed neutral with water, dried over sodium sulphate and evaporated under reduced pressure. The residual oily 2-chloro-4-methoxy-3,5,6-trimethyl-benzene boils at 77°–79° C./1 mm Hg.

65.35 g. of 2-chloro-4-methoxy-3,5,6-trimethyl-benzene are mixed with 235 ml. of acetic acid, 446 ml. of aqueous hydrochloric acid [37 g/v] and 107 ml. of aqueous formaldehyde (35% by weight). The mixture is stirred at 70° C. for 3 hours and, after cooling, introduced into 2000 ml. of water. The aqueous solution is extracted three times with 1000 ml. of methylene chloride. The methylene chloride extract is washed three times with 1000 ml. of water, dried over sodium sulphate and evaporated. The residual 2-chloro-4-methoxy-3,5,6-trimethyl-benzyl chloride is purified by adsorption on silica gel using low boiling petroleum ether for the elution. The compound melts at 59°–63° C. after recrystallisation from low boiling petroleum ether.

70.8 g. of 2-chloro-4-methoxy-3,5,6-trimethyl-benzyl chloride are dissolved in 500 ml. of toluene. The solution is treated with 77 g. of triphenylphosphine and stirred at 100° C. for 18 hours. The 2-chloro-4-methoxy-3,5,6-trimethyl-benzyl-triphenylphosphonium chloride which separates in the form of white crystals is washed with diethyl ether and dried in vacuo. The phosphonium salt melts at 215° C.

EXAMPLE 3

After the addition of a small amount of iron (III) nitrate, 2700 ml. of liquid ammonia are treated portionwise with 169.5 g. of potassium while stirring and cooling. As soon as the initially blue colour has disappeared (i.e., after about 30–45 minutes), acetylene gas is introduced in a stream of three liters per minute until the dark colour of the mixture becomes lighter. Then the gas stream is reduced to two liters per minute and the mixture treated dropwise with a solution of 500 g. of methylglyoxal dimethylacetal in 425 ml. of absolute ether. The gassing with acetylene is continued for a further 1 hour while stirring. The mixture is subsequently treated portionwise with 425 g. of ammonium chloride, gradually warmed to 30° C. within 12 hours while evaporating the ammonia and extracted with 1600 ml. of diethyl ether. The ether extract is dried over sodium sulphate and evaporated under reduced pressure. The residual 4,4-dimethoxy-3-methyl-but-1-yne-3-ol boils, after rectification, at 33° C./0.03 mmHg; $n_D^{25} = 1.4480$.

198 g. of 4,4-dimethoxy-3-methyl-but-1-yne-3-ol are dissolved in 960 ml. of high boiling petroleum ether and, after the addition of 19.3 g. of 5% palladium catalyst and 19.3 g. of quinoline, hydrogenated under normal conditions. After the uptake of 33.5 liters of hydrogen, the hydrogenation is terminated. The catalyst is filtered off. The filtrate is evaporated under reduced pressure. The residual 4,4-dimethoxy-3-methyl-but-1-en-3-ol boils, after rectification, at 70°–72° C./18 mm Hg.

195 ml. of phosgene are introduced into 1570 ml. of carbon tetrachloride at −10° C. After the addition of 213 g. of pyridine, the solution is treated dropwise with 327 g. of 4,4-dimethoxy-3-methyl-but-1-en-3-ol at a temperature of −10° C. to −20° C. The mixture is slowly warmed to 25° C. while stirring, stirred for a further 3 hours at room temperature, cooled to 15° C. and treated with 895 ml. of water. The aqueous phase is separated and discarded. After standing for 12 hours in the cold, the organic phase is treated with 448 ml. of 5% by weight aqueous sulphuric acid, stirred for 5 hours, then washed with water, dried over sodium sulphate and evaporated under reduced pressure. The residual 2-formyl-4-chloro-but-2-ene boils, after rectification, at 37°–40° C./1.8 mm Hg; $n_D^{25}=1.4895$.

165.7 g. of 2-formyl-4-chloro-but-2-ene are dissolved in 840 ml. of benzene and treated with 367 g. of triphenylphosphine. The mixture is heated to boiling under reflux conditions for 12 hours while gassing with nitrogen and then cooled to 20° C. The precipitated 2-formyl-but-2-ene-4-triphenylphosphonium chloride melts at 250°–252° C. after washing with benzene and drying.

212.6 g. of 2-formyl-but-2-ene-4-triphenylphosphonium chloride and 95 g. of 3-formyl-crotonic acid ethyl ester are introduced into 1100 ml. of butanol and treated at 5° C. with a solution of 57 g. of triethylamine in 60 ml. of butanol. The mixture is subsequently stirred for 6 hours at 25° C., then cooled, introduced into water and thoroughly extracted with hexane. The hexane phase is first washed repeatedly with methanol/water (6:4 parts by volume), then washed with water, dried over sodium sulphate and filtered. The filtrate is isomerised by shaking with iodine for 12 hours. The iodine is removed by the addition of sodium thiosulphate. The filtrate is washed with water again, dried and evaporated under reduced pressure. The residual 7-formyl-3-methyl-octa-2,4,6-trien-1-oic acid ethyl ester can be used in the process without further purification.

EXAMPLE 4

39 g. of 2,6-dichloro-4-methoxy-benzyl-triphenylphosphonium chloride and 16 g. of 7-formyl-3-methyl-octa-2,4,6-trien-1-oic acid ethyl ester are heated at 82°–85° C. under reflux conditions while stirring for 2 hours after the addition of 40 g. of 1,2-butylene oxide. The mixture is then thoroughly extracted with hexane. The hexane extract is washed several times with methanol/water (60:40 parts by volume), dried over sodium sulphate and evaporated under reduced pressure. The residue is purified by absorption on silica gel using hexane for the elution. The 9-(2,6-dichloro-4-methoxyphenyl)-3,7-dimethyl-nona-2,4,6,8-tetraen-1-oic acid ethyl ester obtained from the eluate melts at 117°–118° C. after recrystallisation from hexane.

EXAMPLE 5

77 g. of 3,5-dichloro-anisole are dissolved in 250 ml. of ether. After the addition of 70 ml. of aqueous formaldehyde [35% g/v], the solution is gassed with hydrogen chloride at room temperature while stirring for 8 hours. The solution is subsequently poured on to ice and thoroughly extracted with diethyl ether. The ether extract is washed neutral with water, dried over sodium sulphate and evaporated under reduced pressure. The residual oily 2,6-dichloro-4-methoxy-benzyl chloride has a refractive index of $n_D^{24}=1.5730$.

23.7 g. of 2,6-dichloro-4-methoxy-benzyl chloride, 26.2 g. of triphenylphosphine and 150 ml. of absolute benzene are heated for 12 hours under reflux conditions. The 2,6-dichloro-4-methoxy-benzyl-triphenylphosphonium chloride which precipitates on cooling is dried in vacuo before being used in the process.

EXAMPLE 6

By the procedure of Example 1, 2-chloro-4-methoxy-5,6-dimethyl-benzyltriphenylphosphonium chloride is reacted with 7-formyl-3-methyl-octa-2,4,6-trien-1-oic acid ethyl ester to obtain 9-(2-chloro-4-methoxy-5,6-dimethyl-phenyl)-3,7-dimethyl-nona-2,4,6,8-tetraen-1-oic acid ethyl ester, a yellow-red oil.

The 2-chloro-4-methoxy-5,6-dimethyl-benzyl-triphenylphosphonium chloride used as the starting material is prepared in a manner analogous to that described in Examples 2 and 6, starting, for example, from 2,3-dimethyl-aniline and proceeding via 2,3-dimethyl-5-nitro-aniline, 2,3-dimethyl-5-nitro-phenyl, 2,3-dimethyl-5-nitro-anisol, 2,3-dimethyl-5-amino-anisole, 2,3-dimethyl-5-chloro-anisole and 2-chloro-4-methoxy-5,6-dimethyl-benzyl chloride.

EXAMPLE 7

By the procedure of Example 1, 2,3,6-trichloro-4-methoxy-benzyltriphenyl-phosphonium chloride is reacted with 7-formyl-3-methyl-octa-2,4,6-trien-1-oic acid ethyl ester to obtain 9-(2,3,6-trichloro-4-methoxyphenyl)-3,7-dimethyl-nona-2,4,6,8-tetraen-1-oic acid ethyl ester of melting point 126°–128° C.

The 2,3,6-trichloro-4-methoxy-benzyl-triphenylphosphonium chloride used as the starting material can be prepared in a manner analogous to that described in Examples 2 and 5 starting, for example, from 2,3,5-trichloro-phenol and proceeding via 2,3,5-trichloro-anisole and 2,3,6-trichloro-4-methoxy-benzyl chloride.

EXAMPLE 8

By the procedure of Example 1, 2,4-dimethoxy-3,6-dimethyl-benzyltriphenyl-phosphonium chloride is reacted with 7-formyl-3-methyl-octa-2,4,6-trien-1-oic acid ethyl ester to obtain 9-(2,4-dimethoxy-3,6-dimethyl-phenyl)-3,7-dimethyl-nona-2,4,6,8-tetraen-1-oic acid ethyl ester.

The 9-(2,4-dimethoxy-3,6-dimethyl-phenyl)-3,7-dimethyl-nona-2,4,6,8-tetraen-1-oic acid obtained by saponifying the foregoing ester melts at 214°–215° C.

The 2,4-dimethoxy-3,6-dimethyl-benzyl-triphenylphosphonium chloride used as the starting material can be prepared in a manner analogous to that described in Example 2 starting, for example, from orcin (3,5-dihydroxy-toluene) and proceeding via 2-acetyl-3,5-dihydroxy-toluene, 2-acetyl-3,5-dihydroxy-p-xylol, 2,6-dihydroxy-p-xylol, 2,6-dimethoxy-p-xylol and 2,4-dimethoxy-3,6-dimethyl-benzyl chloride.

EXAMPLE 9

By the procedure of Example 1, 6-chloro-4-methoxy-2,5-dimethyl-benzyl-triphenylphosphonium chloride is reacted with 7-formyl-3-methyl-octa-2,4,6-trien-1-oic acid ethyl ester to obtain 9-(6-chloro-4-methoxy-2,5-dimethyl-phenyl)-3,7-dimethyl-nona-2,4,6,8-tetraen-1-oic acid ethyl ester of melting point 106°–107° C.

The 6-chloro-4-methoxy-2,5-dimethyl-benzyl-triphenylphosphonium chloride used as the starting material can be prepared in a manner analogous to that described in Examples 2 and 5, starting, for example, from 3-chloro-2,5-dimethyl-nitrobenzene and proceeding via 3-chloro-2,5-dimethyl-aniline, 3-chloro-2,5-dimethyl-phenyl, 3-chloro-2,5-dimethyl-anisole and 6-chloro-4-methoxy-2,5-dimethyl-benzyl chloride.

EXAMPLE 10

41 g. of 9-(6-chloro-4-methoxy-2,5-dimethyl-phenyl)-3,7-dimethyl-nona-2,4,6,8-tetraen-1-oic acid ethyl ester are dissolved in 750 ml. of ethanol. The solution is treated with 41 g. of potassium hydroxide in 63 ml. of water, heated to boiling for 30 minutes under a nitrogen atmosphere, cooled, introduced into water and acidified with hydrochloric acid. The precipitated 9-(6-chloro-4-methoxy-2,5-dimethyl-phenyl)-3,7-dimethyl nona-2,4,6,8-tetraen-1-oic melts at 231°–234° C.

EXAMPLE 11

15 g. of 9-(6-chloro-4-methoxy-2,5-dimethyl-phenyl)-3,7-dimethyl-nona-2,4,6,8-tetraen-1-oic acid are dissolved in 750 ml. of tetrahydrofuran. The solution obtained is treated with 2.64 ml. (0.7 mol) of phosphorus trichloride, concentrated after 12 hours to half of its volume at 30° C. under reduced pressure and added dropwise at 0°–5° C. to a tetrahydrofuran solution containing 14.6 g. of ethylamine. The mixture is stirred for 1 hour at room temperature, introduced into a saturated aqueous sodium chloride solution and extracted with methylene chloride. The extract is washed with an aqueous sodium chloride solution, dried and evaporated under reduced pressure. The residual 9-(6-chloro-4-methoxy-2,5-dimethyl-phenyl)-3,7-dimethyl-nona-2,4,6,8-tetraen-1-oic acid ethyl amide is purified by adsorption on silica gel using methylene chloride/methanol (90:10 parts by volume) for the elution. After recrystallisation from ethyl acetate, this ethyl amide melts at 202° C. to 203° C.

EXAMPLE 12

A capsule is prepared containing the following ingredients:

| | | |
|---|---|---|
| 9-(2-Chloro-4-methoxy-3,5,6-trimethyl-phenyl)-3,7-dimethyl-nona-2,4,6,8-tetraen-1-oic acid ethyl ester | 10 | mg. |
| Wax mixture | 41.5 | mg |
| Vegetable oil | 98.0 | mg. |
| Trisodium salt of ethylenediaminetetraacetic acid | 0.5 | mg. |
| Individual weight of a capsule | 150 | mg. |
| Active ingredient content of a capsule | 10 | mg. |

EXAMPLE 13

A salve is prepared containing 2.0% of active ingredient with the following ingredients:

| | |
|---|---|
| 9-(2-Chloro-4-methoxy-3,5,6-trimethyl-phenyl)-3,7-dimethyl-nona-2,4,6,8-tetraen-1-oic acid ethyl ester | 2.0 g. |
| Cetyl alcohol | 2.7 g. |
| Lanolin | 6.0 g. |
| Petroleum jelly | 15.0 g. |
| Distilled water q.s. ad | 100.0 g. |

We claim:

1. A compound of the formula:

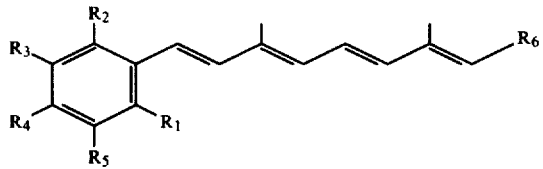

wherein one of $R_1$ and $R_2$ is halogen or lower alkyl, and the other is halogen or lower alkoxy; $R_3$ and $R_5$ are hydrogen, halogen or lower alkyl; with the proviso that one of $R_3$ and $R_5$ is other than halogen; $R_4$ is halogen, lower alkoxy, amino, mono(lower alkyl)amino or di(lower alkyl) amino; and $R_6$ is formyl, hydroxymethyl, or alkoxymethyl and salts thereof.

* * * * *